United States Patent [19]

Yoshida

[11] Patent Number: 5,061,253
[45] Date of Patent: Oct. 29, 1991

[54] FLUID-COMMUNICATING DEVICE WITH VALVE FUNCTION
[75] Inventor: Toshiki Yoshida, Osaka, Japan
[73] Assignee: Nissho Corporation, Osaka, Japan
[21] Appl. No.: 429,233
[22] Filed: Oct. 24, 1989
[30] Foreign Application Priority Data
Nov. 14, 1988 [JP] Japan .................. 63-286987
[51] Int. Cl.⁵ ............................................. F16L 37/28
[52] U.S. Cl. ................................ 604/246; 604/236; 604/256; 251/342
[58] Field of Search ................. 604/99, 246, 247, 249, 604/256, 236; 128/207.15; 137/843; 251/149, 149.1, 149.8, 342

[56] References Cited
U.S. PATENT DOCUMENTS

| | | |
|---|---|---|
| 3,570,484 | 3/1971 | Steer .................. 604/249 |
| 3,901,246 | 8/1975 | Wallace ............... 251/342 |
| 4,018,231 | 4/1977 | Wallace ............. 128/207.15 |
| 4,147,170 | 4/1979 | Taylor .............. 128/207.15 |
| 4,429,856 | 2/1984 | Jackson ............... 604/247 |
| 4,449,693 | 5/1984 | Gereg ................. 604/236 |
| 4,710,168 | 12/1987 | Schwab et al. .......... 604/99 |
| 4,722,727 | 2/1988 | Ogden ................. 604/30 |
| 4,915,687 | 4/1990 | Sivert ................ 604/249 |

FOREIGN PATENT DOCUMENTS
2001146A 7/1978 United Kingdom .

Primary Examiner—Stephen C. Pellegrino
Assistant Examiner—Ralph A. Lewis
Attorney, Agent, or Firm—Armstrong, Nikaido, Marmelstein, Kubovcik & Murray

[57] ABSTRACT

A fluid-communicating device with valve function comprising a tubular body having an inlet and an outlet, and a blocking body inserted in the tubular body is disclosed. The blocking body comprises a plug portion, and a supporting portion on which a diameter-enlarging portion for enlarging an inner wall of the tubular body is provided. The plug portion of the blocking body is placed in a seal portion of the tubular body to close the tubular body and to prevent the passage of fluid. In use, a tip of a syringe and the like is inserted into the tubular body, so that there is formed a clearance between the outer wall of the plug portion and the inner wall of the seal portion. Fluid passes through the clearance and a fluid passage formed longitudinally on the supporting portion or on an inner wall of the tubular body.

7 Claims, 4 Drawing Sheets

FLUID-COMMUNICATING DEVICE WITH VALVE FUNCTION

BACKGROUND OF THE INVENTION

The present invention relates to a fluid-communicating device with valve function, and more particularly to a fluid-communicating device with valve function which, in use, receives the insertion of a tip of a syringe and the like into an inlet of the device and communicates the inlet with an outlet, whereby enabling the fluid passage from the inlet to the outlet, or from the outlet to the inlet. Such communication is impossible before the insertion of the tip.

In medical devices such as balloon catheters or endotracheal tubes having a balloon, there has been used a tube shown in FIG. 6 having a plug at an injection/discharge port of the tube, or a tube shown in FIG. 7 having a valve which opens only on injecting or discharging fluid, when injecting or discharging fluid such as gas or liquid into or from the balloon. When injecting or discharging fluid with the use of the former tube with the plug, the plug 22 is removed from the injection/discharge port while, for example, pinching the tube 21 with fingers to prevent the leakage of fluid in the balloon due to energizing force of the balloon. Then, a tip of a syringe and the like is inserted into the injection port of the tube. The latter tube with the valve comprises a casing 31, a valve disc 32, a spring 33 and a rubber packing 34. On injecting or discharging fluid, the communication from an inlet to an outlet of the tube is made possible only by inserting a tip of a syringe into the inlet 35 of the tube.

However, these conventional techniques have the following problems. That is, in the case of the former tube with the plug, it requires a troublesome operation of pinching the tube with fingers, and there is a risk of fluid leakage when removing the plug. The latter tube solves the above-mentioned problems inherent in the former tube. But, the assembly of the valve is time-consuming and cost for the valve becomes large, because many parts are necessary for assembly of the valve. Further, since a metal spring is employed in the valve, there is a danger that the spring rusts away and fails to function.

The present invention was made to solve the above-mentioned drawbacks, and it is an object of the present invention to provide a fluid-communicating device with valve function of which assembly is easy and which can prevent leakage of fluid when injecting or discharging fluid.

SUMMARY OF THE INVENTION

In accordance with the present invention, there is provided a fluid-communicating device with valve function comprising:

(A) a tubular body made of soft material both ends thereof being open, the tubular body having an inlet and an outlet, and comprising
   a tip-receiving portion of which diameter is tapered down from the inlet to the outlet,
   a seal portion extending from the tip-receiving portion to the outlet of the tubular body and having an inner diameter which is approximately the same as an inner diameter of an end of the tip-receiving portion on the side of the outlet, and
   a fixing portion extending from the seal portion to the outlet of the tubular body, and (B) a blocking body made of hard material and being inserted and supported in the tubular body, the blocking body comprising
   a column-like plug portion placed in the tubular body in the way which the plug portion closely contacts with the seal portion of the tubular body, and having an outer diameter which is slightly larger than an inner diameter of the seal portion, and
   a column-like supporting portion engaging with an inner surface of the fixing portion and being held in the fixing portion wherein a diameter-enlarging means for enlarging an end of an inner wall of the fixing portion and a part of an inner wall of the seal portion adjoining the end of the fixing portion is provided adjacent or near an end of the fixing portion on the side of the seal portion; and a fluid passage for communicating the inlet with the outlet during the use of the device is formed longitudinally on the fixing portion or on the supporting portion.

According to the device having the above-mentioned structure, fluid can easily pass from an inlet of the fluid-communicating device to an outlet of the same by using a syringe with a tip having an outer diameter sufficiently larger than the outer diameter of a plug portion of a closing body. That is, when the tip of the syringe is inserted into the inlet of the device, the diameter of a tip-receiving portion of a tubular body is enlarged because the device is made of soft materials such as, for example, soft polyvinyl chloride or polyethylene. Then, the seal portion having the same inner diameter as that of a diameter-reduced end of the tip-receiving portion is also enlarged so that a clearance, i.e. a fluid passage, is formed between the plug portion of the closing body and the seal portion of the tubular body. Fluid is injected into or discharged from the device through such fluid passage.

DETAILED DESCRIPTION

Next, a fluid-communicating device with valve function of the present invention is explained based on the attached drawings.

Figure 1:
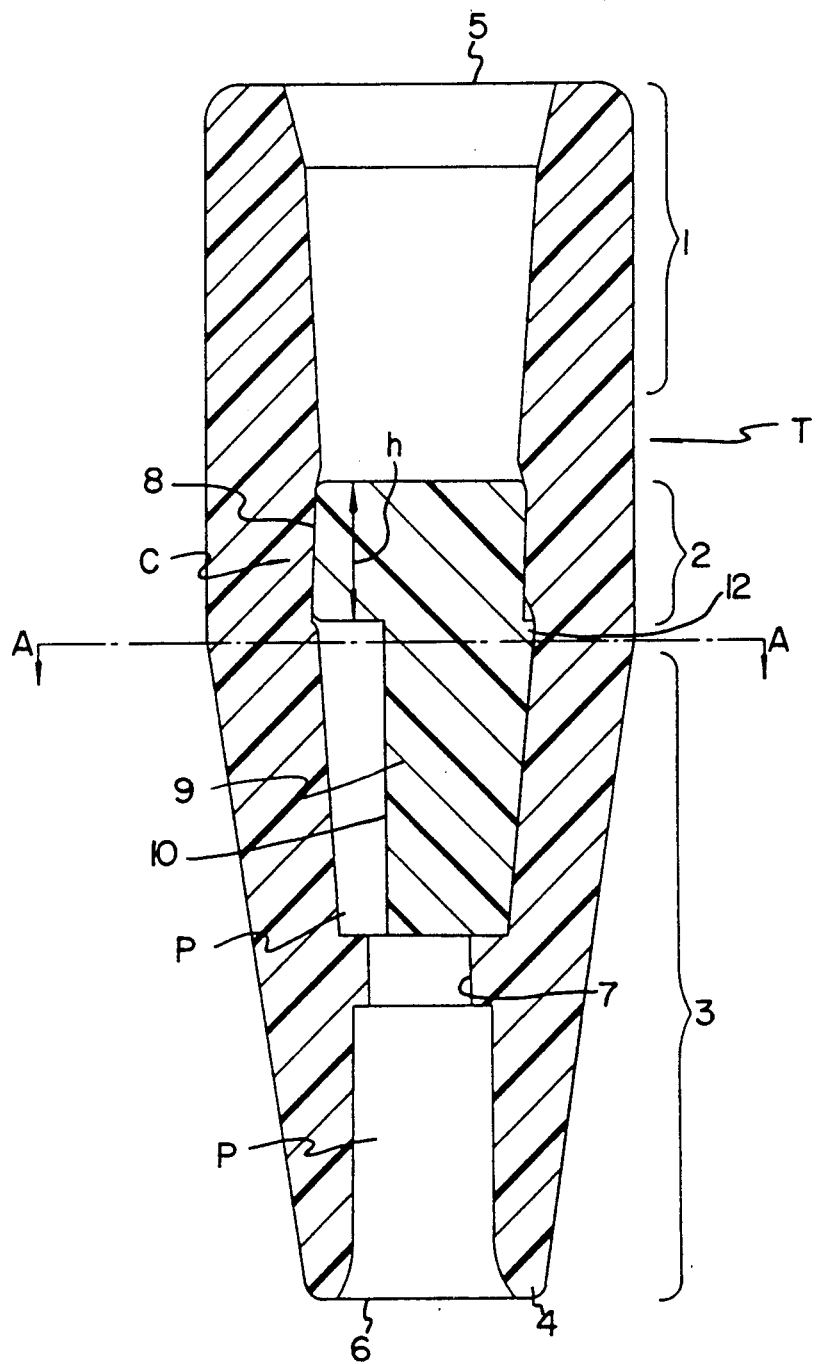
FIG. 1 is a longitudinal sectional view of an embodiment of a fluid-communicating device with valve function of the present invention comprising a tubular body with an annular projection, and a blocking body with a bulged portion and a groove all over a supporting portion.
Figure 2A:
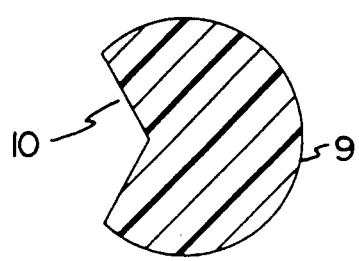
FIG. 2a is a sectional view of the closing body in FIG. 1 taken along the line A—A.
Figure 2B:
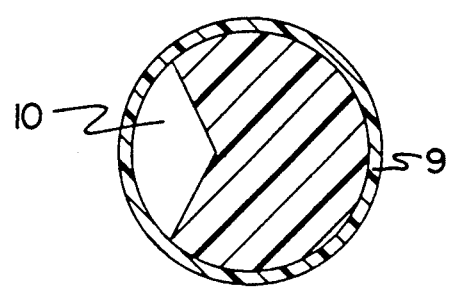
FIG. 2b is a sectional view, similar to FIG. 2a, of another embodiment of a closing body wherein a ring is in use as diameter-enlarging means.

As shown in FIGS. 1 to 3, a fluid-communicating device with valve function (hereafter referred to as fluid-communicating device) of the present invention comprises a tubular body T made of soft materials and a blocking body C made of hard materials. The blocking body C is inserted into a hollow portion of the tubular body T to close the hollow portion. In the tubular body T, a diameter-enlarging means for enlarging an end of an inner wall of a fixing portion 3 and a part of an inner wall of a seal portion 2 adjoining the end of the fixing portion 3 is provided adjacent or near the end of the fixing portion 3 on the side of the seal portion 2. Further, a fluid passage P for communicating an inlet 5 with an outlet 6 during the use of the fluid-communicating device is longitudinally formed on the fixing portion 3 or a supporting portion 9 mentioned later. The tubular body T, both ends thereof are made open, is a tubular member made of soft materials such as polyethylene, soft polyvinyl chloride, ethylene vinyl acetate copolymer, rubber, and elastomer. The tubular body T has an inlet 5 and an outlet 6. A tip-receiving portion 1, the seal portion 2, and the fixing portion 3 are formed in this order from the inlet 5 to the outlet 6.

The tip-receiving portion 1 serves to receive a nozzle portion of a syringe and the like, so-called a tip, inserted into the tubular body T. The tip-receiving portion 1 has a hollow portion of which inner diameter is tapered down from the inlet 5 to the outlet 6. The tip-receiving portion 1 is radially outwardly enlarged when the tip is inserted into the tubular body T since the tubular body T is made of soft materials.

The seal portion 2 serves to closely contact with a plug portion 8 of a blocking body C mentioned later in order to block the hollow portion of the tubular body T, and to prevent passage of fluid from the inlet 5 to the outlet 6, or from the outlet 6 to the inlet 5. Inner diameter of the seal portion 2 is designed to be the same as an inner diameter of an end of the tip-receiving portion 1 on the side of the outlet 6.

Figure 4:
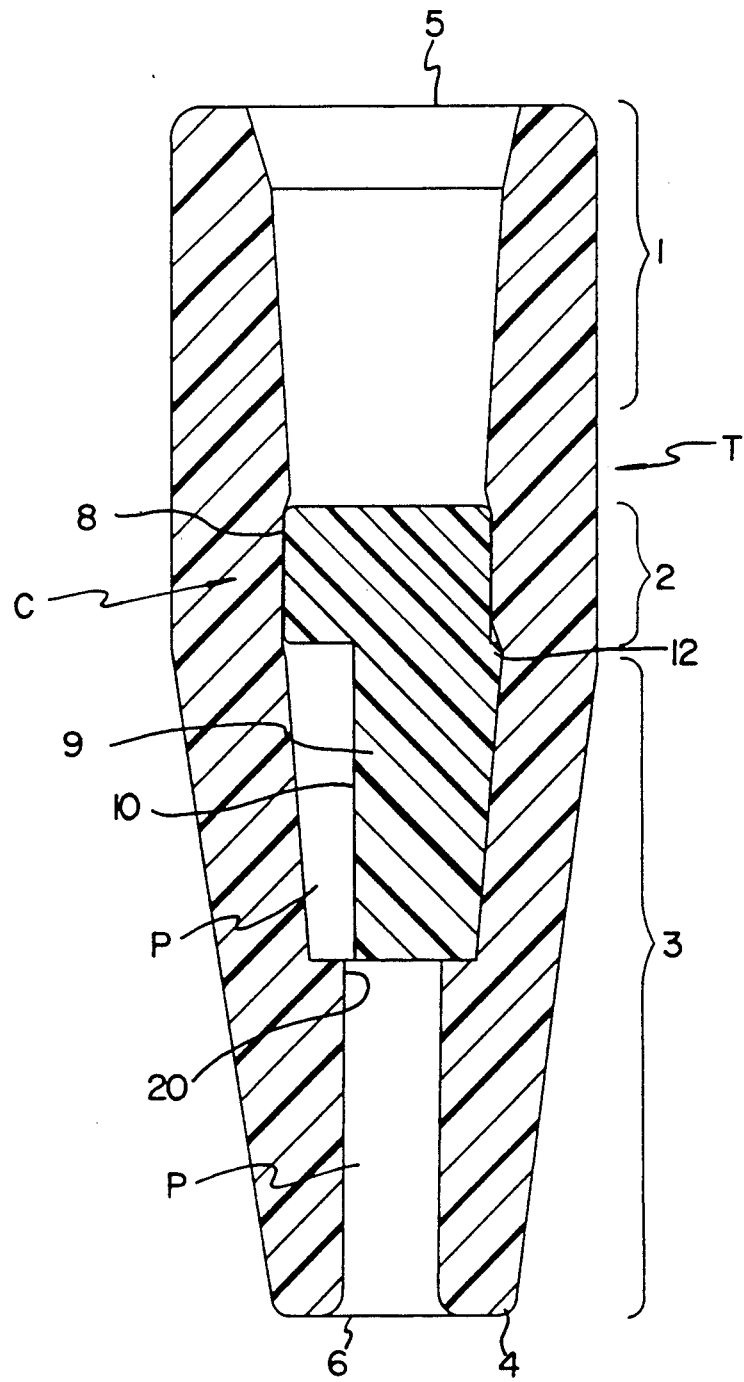
FIG. 4 is a longitudinal sectional view of another embodiment of a fluid-communicating device with valve function of the present invention employing a stepped portion instead of an annular projection at a fixing portion.
Figure 7:
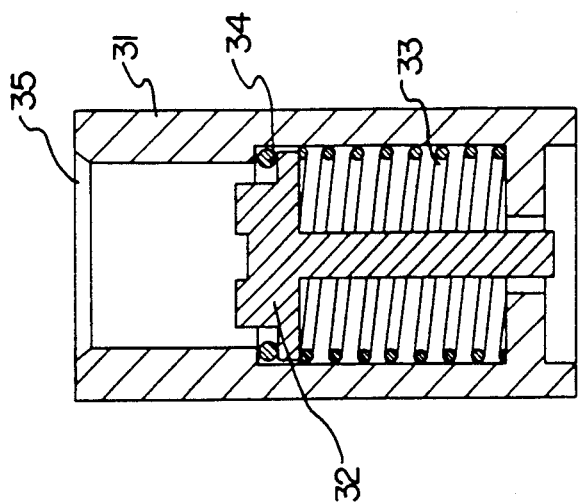
FIGS. 6 and 7 are schematic views of conventional devices.
Figure 6:
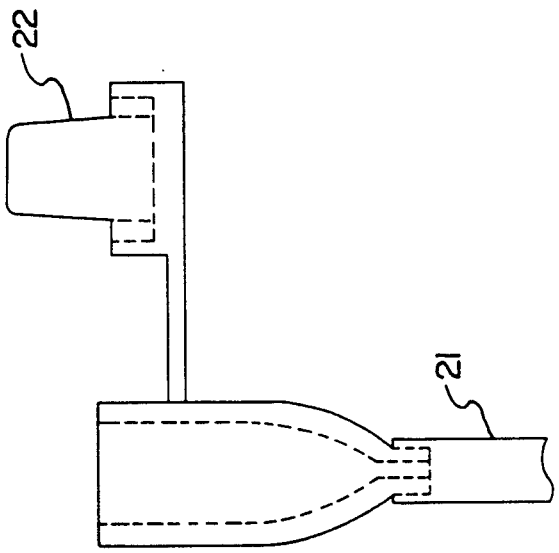

The fixing portion 3 extending from the seal portion 2 to the outlet 6 of the tubular body T engages with a supporting portion 9 of the blocking body C and serves to fix the blocking body C to the hollow portion of the tubular body T. The engagement (including close contact) is mainly carried out by the inner wall of the fixing portion 3 and the outer wall of the supporting portion 9. It is desirable to provide an annular projection 7 (see FIG. 1) or a stepped portion 20 (see FIG. 4) as occasion demands on the outlet side of the fixing portion 3, since the lower end of the supporting portion 9 can be engaged with the annular projection 7 or stepped portion 20 whereby the blocking body C can be surely fixed to a predetermined position. Medical devices such as balloon catheters are connected to an end 4 of the fixing portion 3 on the side of the outlet 6 using a connector if need be. In the device shown in FIG. 1, inner diameter of the outlet 6 is slightly enlarged toward its end for the sake of forming (i.e. centering).

The blocking body C comprises a plug portion 8 and a supporting portion 9, and is made of hard materials such as polypropylene, polyamide, polystyrene, polycarbonate, and acrylonitrile-butadien-styrene copolymer. The blocking body C is so arranged in the tubular body T that the plug portion 8 closely contacts with the seal portion 2 and that the supporting portion 9 engages with the fixing portion 3.

The plug portion 8 serves to closely contact with the seal portion 2 and to close a hollow portion of the tubular body T, i.e. a fluid passage P. The plug portion 8 is a short column-like part having an outer diameter slightly larger than the inner diameter of the seal portion 2 in order to surely block the fluid passage P.

The supporting portion 9 supports the plug portion 8, and prevents the movement of the blocking body C toward the outlet 6 by engaging with the inner wall of the fixing portion 3 of the tubular body T. It is desirable to provide an annular projection 7 or a stepped portion 20 on the outlet side of the fixing portion 3 in order to surely prevent the movement of the blocking body C and surely fix the blocking body C to a predetermined position. In the fluid-communicating device of FIG. 1, an end of the supporting portion 9 on the side of the outlet 6 closely contacts with the annular projection 7. The shape and size of the supporting portion 9 are not particularly limited in the present invention as long as the inlet 5 surely communicates with the outlet 6 when the fluid-communicating device is in use, that is, a nozzle of a syringe and the like (hereafter referred to as tip) is inserted into the tip-receiving portion 1. However, they are limited by the shape and size of the diameter-enlarging means, fluid passage P, and fixing portion 3.

Figure 3A:
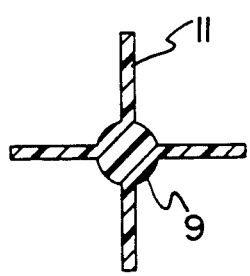
FIG. 3a is a sectional view, similar to FIG. 2a, of another embodiment of a closing body.
Figure 3B:
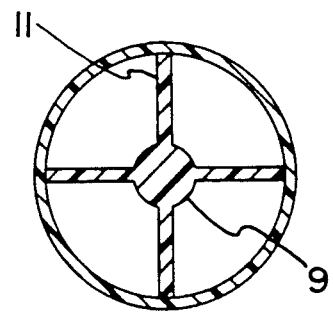
FIG. 3b is a sectional view, similar to FIG. 2a of still another embodiment of a closing body wherein a wring is used as a diameter-enlarging means.

The diameter-enlarging means is compulsorily inserted into such a position as is adjacent an end of the fixing portion on the side of the seal portion 2, and serves to enlarge an end of an inner wall of the fixing portion 3 and a part of an inner wall of the seal portion 2 adjoining the end of the fixing portion 3. By enlarging a part of an inner wall of the seal portion 2, the plug portion 8 having a large height or thickness h (see FIG. 1) can be inserted into the seal portion 2. In result, the seal performance becomes stable since the seal length can be increased. Concrete examples of the diameter-enlarging means are, for instance, ribs 11 formed longitudinally on the supporting portion 9, a substantially column-like bulged portion 12 formed on at least an end of the supporting portion on the side of the plug portion 8, and a ring (not shown) put on the fixing portion 3 close to the seal portion 2. At least an end of the rib 11 on the side of the plug portion 8 projects radially outwardly from an outer wall of the plug portion 8 and an inner wall of the fixing portion 3. The projecting portion enlarges the inner wall of the fixing portion 3 and a part of an inner wall of the seal portion 2. The number of ribs 11 is not limited in the present invention, and might be one or more. In general, two to five ribs are provided symmetrically with respect to a longitudinal axis of the tubular body T. FIGS. 3a and 3b show a supporting portion 9 having four ribs 11.

At least an end of the bulged portion 12 adjoining the plug portion 8 or the whole bulged portion 12 projects radially outwardly from an outer wall of the plug portion 8 and an inner wall of the fixing portion 3. The projecting portion enlarges an inner wall of the tubular body T with which the projecting portion contacts and an inner wall near such contacting portions. The number of projecting portion is not limited in the present invention, and might be one or more. In general, however, the number of the projecting portions is two to five. In the case of a bulged portion 12 having such a shape as to hardly form a fluid passage P between the bulged portion 12 and the fixing portion 3, it is necessary to form a groove longitudinally on the outer wall of the bulged portion 12 or on the inner wall of the fixing portion 3 contacting with the bulged portion 12.

The outer diameter of a ring is so designed as to be larger than the outer diameter of a plug portion 8 and the inner diameter of a fixing portion 3. When a ring is employed as a diameter-enlarging means, it is necessary to form ribs or grooves on a supporting portion 9 longitudinally in order to secure a fluid passage P. The fluid passage P is defined by the inner wall of the fixing portion 3 and the groove 10, by the inner wall of the fixing portion 3, ribs 11 and outer wall of the supporting portion 9, or by the inner wall of the fixing portion 3 and outer wall of the bulged portion 12 near the projecting portion. When the outer diameter of the supporting portion 9 is smaller than the inner diameter of the fixing portion 3, the fluid passage P is such a space as is defined by the inner wall of the fixing portion 3 and the outer wall of the supporting portion 9.

When the annular projection 7 or stepped portion 20 is provided on the outlet side of the fixing portion 3, the depth of the grooves 10 or the height of the ribs 11 should be suitably determined in order to prevent the fluid passage from being closed by the annular projection 6 and the like. That is, in the case of a groove 10, the depth of the groove 10 should be designed that a bottom of the groove 10 is inside the inner wall of the annular projection 7 or stepped portion 20. In the case of a rib 11, the height of the rib 1 should be so designed that a root of the rib 11 is inside the inner wall of the annular projection 7 and the like.

Figure 5:
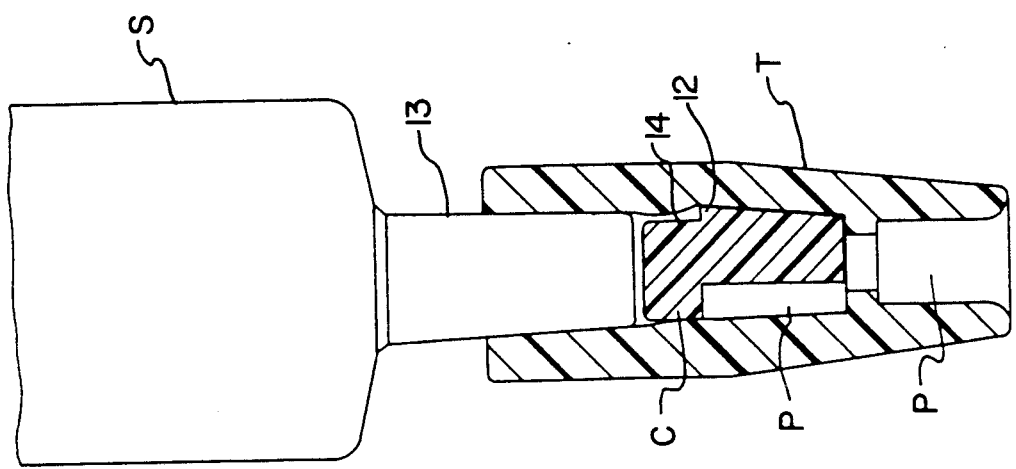
FIG. 5 is a view showing a state wherein a tip of a syringe is inserted into the device of FIG. 1.

Next, method of using a fluid-communicating device of the present invention is explained based on FIG. 5.

Firstly, a tip 13 of a syringe S is inserted into a tip-receiving portion 1 of a fluid-communicating device till an end of the tip 13 contacts with a seal portion 2. Then, the inner diameter of the tip-receiving portion 1 is enlarged. Simultaneously, the inner diameter of the seal portion 2 adjoining the tip-receiving portion 1 and having the same inner diameter as that of the tip-receiving portion 1 is also enlarged, so that a clearance 14 is formed between the seal portion 2 and the plug portion 8. When fluid is injected from the syringe 5 in this condition, the fluid passes through the clearance 14, and a fluid passage P, i.e. a space defined by the fixing portion 3 and the supporting portion 9. The fluid is then injected into a balloon if, for example, a tube communicating with a balloon of a balloon catheter is connected to an outlet of the fluid-communicating device. As a fluid passage P, there can be employed various kinds of modifications such as grooves formed on the whole fixing portion 3 including an annular projection 7 or a stepped portion besides grooves 10 or ribs 11 formed on the supporting portion 9.

As is clear from the above-mentioned explanation, the fluid-communicating device of the present invention has the following advantages.

(1) The fluid-communicating device of the present invention is easy to produce and is economical since the number of parts is small.

(2) Fluid does not leak on the injection or discharge thereof.

(3) The structure of the fluid-communicating device is simple and the rusting and the like does not occur, so that the performance of the device is stable.

What is claimed is:

1. A fluid-communicating device with valve function comprising:

a tubular body made of soft material both ends thereof being open, providing for an inlet and outlet, and comprising a tip-receiving portion extending from the inlet of the tubular body of which inner diameter is tapered down from an inlet end toward an outlet end, a seal portion extending from the tip-receiving portion toward the outlet of the tubular body and having an inner diameter which is approximately the same as the inner diameter of the outlet end of the tip-receiving portion, and a fixing portion extending from the seal portion to the outlet of the tubular body, and a blocking body made of hard material and being inserted and supported in the tubular body, the blocking body comprising a column-like plug portion placed in the tubular body whereby the plug portion closely contacts with the seal portion of the tubular body, and having an outer diameter which is slightly larger than the inner diameter of the seal portion, and a column-like supporting portion annularly engaging with an inner surface of the fixing portion and being held in the fixing portion wherein a diameter-enlarging means for enlarging an end of an inner wall of the fixing portion and a part of an inner wall of the seal portion adjoining the end of the fixing portion is provided in close proximity to the end of the fixing portion adjacent to the seal portion; and a fluid passage for communicating the tubular body inlet with the tubular body outlet during the use of the device is formed longitudinally on one of the fixing portion and the supporting portion, wherein the diameter-enlarging means is at least one rib formed longitudinally on the supporting portion, and at least an end of the rib adjacent to the plug portion projects radially outwardly from an outer wall of the plug portion.

2. A fluid-communicating device with valve function comprising:

a tubular body made of soft material both ends thereof being open, providing for an inlet and outlet, and comprising a tip-receiving portion extending from the inlet of the tubular body of which inner diameter is tapered down from an inlet end toward an outlet end, a seal portion extending rom the tip-receiving portion toward the outlet of the tubular body and having an inner diameter which is approximately the same as the inner diameter of the outlet end of the tip-receiving portion, and a fixing portion extending from the seal portion to the outlet of the tubular body, and a blocking body made of hard material and being inserted and supported in the tubular body, the blocking body comprising a column-like plug portion placed in the tubular body the plug portion closely contacting with the seal portion of the tubular body, and having an outer diameter which is slightly larger than the inner diameter of the seal portion, and a column-like supporting portion annularly engaging with an inner surface of the fixing portion and being held in the fixing portion wherein a diameter-enlarging means for enlarging an end of an inner wall of the fixing portion and a part of an inner wall of the seal portion adjoining the end of the fixing portion is provided, in close proximity to the end of the fixing portion adjacent to the seal portion; and a fluid passage for communicating the tubular body inlet with the tubular body outlet during the use of the device is formed longitudinally on at least one of the fixing portion and the supporting portion, wherein the diameter-enlarging means is a bulged portion formed on at least an end of the supporting portion adjacent to the plug portion, and at least an end of the bulged portion adjoining the plug portion projects radially outwardly from an outer wall of the plug portion.

3. A fluid-communicating device with valve function comprising:
   a tubular body made of soft material both ends thereof being open, providing for an inlet and outlet, and comprising
      a tip-receiving portion extending from the inlet of the tubular body of which inner diameter is tapered down from an inlet end toward an outlet end,
      a seal portion extending from the tip-receiving portion toward the outlet of the tubular body and having an inner diameter which is approximately the same as the inner diameter of the outlet end of the tip-receiving portion, and
      a fixing portion extending from the seal portion to the outlet of the tubular body, and
   a blocking body made of hard material and being inserted and supported in the tubular body, the blocking body comprising
      a column-like plug portion placed in the tubular body the plug portion closely contacting with the seal portion of the tubular body, and having an outer diameter which is slightly larger than the inner diameter of the seal portion, and
      a column-like supporting portion annularly engaging with an inner surface of the fixing portion and being held in the fixing portion
   wherein a diameter-enlarging means for enlarging an end of an inner wall of the fixing portion and a part of an inner wall of the seal portion adjoining the end of the fixing portion is provided in close proximity to the end of the fixing portion adjacent to the seal portion; and a fluid passage for communicating the tubular body inlet with the tubular body outlet during the use of the device is formed longitudinally on at least one of the fixing portion and the supporting portion, wherein the diameter-enlarging means is a substantially column-like bulged portion formed on at least an end of the supporting portion adjacent to the plug portion; at least an end of the bulged portion adjoining the plug portion projects radially outwardly from an outer wall of the plug portion; and at least one groove is formed longitudinally on the outer wall of the bulged portion or on the inner wall of the fixing portion closely contacting with the bulged portion.

4. The device of claims 2 or 3 wherein at least one groove is formed longitudinally on the supporting portion.

5. The device of claims 2 or 3, wherein at least one groove is formed longitudinally on the fixing portion.

6. A fluid-communicating device with valve function comprising:
   a tubular body made of soft material both ends thereof being open, providing for an inlet and outlet, and comprising
      a tip-receiving portion of which inner diameter is tapered down from an inlet end toward an outlet end,
      a seal portion extending from the inlet of the tubular body extending from the tip-receiving portion toward the outlet of the tubular body and having an inner diameter which is approximately the same as the inner diameter of the outlet end of the tip-receiving portion, and
      a fixing portion extending from the seal portion to the outlet of the tubular body, and
   a blocking body made of hard material and being inserted and supported in the tubular body, the blocking body comprising
      a column-like plug portion placed in the tubular body the plug portion closely contacting with the seal portion of the tubular body, and having an outer diameter which is slightly larger than the inner diameter of the seal portion, and
      a column-like supporting portion annularly engaging with an inner surface of the fixing portion and being held in the fixing portion wherein a diameter-enlarging means for enlarging an end of an inner wall of the fixing portion and a part of an inner wall of the seal portion adjoining the end of the fixing portion is provided in close proximity to the end of the fixing portion adjacent to the seal portion; and a fluid passage for communicating the tubular body inlet with the tubular body outlet during the use of the device is formed longitudinally on at least one of the fixing portion and the supporting portion, wherein the diameter-enlarging means is a ring having an outer diameter larger than an inner diameter of the fixing portion and being formed on the fixing portion close to the seal portion, and at least one rib is formed longitudinally on the supporting portion.

7. A fluid-communicating device with valve function comprising:
   a tubular body made of soft material both ends thereof being open, providing for a inlet and outlet, and comprising
      a tip-receiving portion extending from the inlet of the tubular body of which inner diameter is tapered down from an inlet end toward an outlet end,
      a seal portion extending from the tip-receiving portion toward the outlet of the tubular body and having an inner diameter which is approximately the same as the inner diameter of the outlet end of the tip-receiving portion, and
      a fixing portion extending from the seal portion to the outlet end of the tubular body, and
   a blocking body made of hard material and being inserted and supported in the tubular body, the blocking body comprising
      a column-like plug portion placed in the tubular body the plug portion closely contacting with the seal portion of the tubular body, and having an outer diameter which is slightly larger than the inner diameter of the seal portion, and
      a column-like supporting portion annularly engaging with an inner surface of the fixing portion and being held in the fixing portion
   wherein a diameter-enlarging means for enlarging an end of an inner wall of the fixing portion and a part of an inner wall of the seal portion adjoining the end of the fixing portion is provided in close proximity to the end of the fixing portion adjacent to the seal portion; and a fluid passage for communicating the tubular body inlet with the tubular body outlet during the use of the device is formed longitudinally on at least one of the fixing portion and the supporting portion, wherein the diameter-enlarging means is a ring having an outer diameter larger than an inner diameter of the fixing portion and being formed on the fixing portion close to the seal portion, and at least one groove is formed longitudinally on the supporting portion.

* * * * *